United States Patent
Doering

(10) Patent No.: US 10,980,721 B2
(45) Date of Patent: Apr. 20, 2021

(54) COSMETIC PRODUCT TO PREVENT BODY ODOR WITH AN IMPROVED LONG-TERM EFFECT

(71) Applicant: Henkel AG & Co. KGaA, Duesseldorf (DE)

(72) Inventor: Thomas Doering, Dormagen (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 15/838,377

(22) Filed: Dec. 12, 2017

(65) Prior Publication Data

US 2018/0168967 A1 Jun. 21, 2018

(30) Foreign Application Priority Data

Dec. 21, 2016 (DE) .................. 10 2016 225 735

(51) Int. Cl.
  *A61K 8/34* (2006.01)
  *A61K 8/37* (2006.01)
  *A61Q 15/00* (2006.01)

(52) U.S. Cl.
  CPC .................. *A61K 8/34* (2013.01); *A61K 8/37* (2013.01); *A61Q 15/00* (2013.01); *A61K 2800/592* (2013.01)

(58) Field of Classification Search
  CPC ...... A61K 8/34; A61K 8/37; A61K 2800/592; A61Q 15/00
  See application file for complete search history.

(56) References Cited

U.S. PATENT DOCUMENTS

| 7,157,411 B2 | 1/2007 | Rohde et al. |
| 2009/0123392 A1 | 5/2009 | Braun et al. |
| 2009/0238787 A1 * | 9/2009 | Finke ...................... A61K 8/34 424/65 |
| 2013/0202543 A1 | 8/2013 | Kueper et al. |
| 2016/0128923 A1 | 5/2016 | Stuhlmann et al. |

FOREIGN PATENT DOCUMENTS

| CN | 107164093 A | 9/2017 |
| DE | 102008043586 A1 | 5/2009 |
| DE | 102013209460 A1 | 11/2014 |
| EP | 1239890 A2 | 9/2002 |
| EP | 2014273 A1 | 1/2009 |
| JP | 2003/113392 * | 4/2003 |

OTHER PUBLICATIONS

Kiyomitsu et al., JP 2003/113392, published: Apr. 18, 2003, English machine translation obtained on Sep. 28, 2018.*
Whitehouse ("Aluminum salts study claims ingredient can be linked with cancer", Updated: Oct. 11, 2016).*
Intellectual Property Office, Search Report under Section 17(5) for United Kingdom Patent Application No. GB1720572.5 dated Aug. 16, 2018.

* cited by examiner

*Primary Examiner* — Genevieve S Alley
(74) *Attorney, Agent, or Firm* — Lorenz & Kopf, LLP

(57) ABSTRACT

The present disclosure relates to cosmetic agents, which in addition to a deodorant agent contain a combination of special aromatic alcohols and certain menthyl compounds. These agents have a long-lasting deodorizing effect. The present disclosure also relates to a cosmetic product that includes the cosmetic agent as contemplated herein, as well as at least one propellant. The present disclosure also relates to the use of the agent as contemplated herein to treat body odor, as well as the use of a combination of aromatic alcohol and menthyl compounds to improve the odor-inhibiting effect of cosmetic agents over a period of from about 24 to about 48 hours.

13 Claims, No Drawings

COSMETIC PRODUCT TO PREVENT BODY ODOR WITH AN IMPROVED LONG-TERM EFFECT

CROSS-REFERENCE TO RELATED APPLICATION

This application claims priority to German Patent Application No. 10 2016 225 735.8, filed Dec. 21, 2016, which is incorporated herein by reference in its entirety.

TECHNICAL FIELD

This application relates to cosmetic compositions containing at least one aromatic alcohol and at least one menthyl compound in addition to an active deodorant ingredient. The use of the combination of an aromatic alcohol and a menthyl compound leads to a significant improvement in the long-term effectiveness against body odor. Excellent neutralization of unpleasant body odor can therefore be achieved even from about 24 to about 48 hours after applying the cosmetic agent as contemplated herein.

BACKGROUND

The present disclosure also relates to a cosmetic product that includes the cosmetic agent as contemplated herein, as well as at least one propellant.

In addition, the present disclosure relates to the use of the cosmetic agent as contemplated herein or the cosmetic product as contemplated herein for the reduction of body odor caused by perspiration.

Finally, the present disclosure relates to the use of a mixture of an aromatic alcohol and a menthyl compound to improve the odor-inhibiting effect of cosmetic products over a period of from about 24 to about 48 hours.

Eccrine and apocrine sweat glands are found in the human armpit. While the eccrine glands produce a watery secretion in response to heat, the apocrine glands produce a viscous secretion in response to stress. This apocrine sweat is a complex mixture, which contains, among other things, steroids, cholesterol and other fats, as well as approximately 10% protein. Unpleasant body odor under the armpit is due to bacterial decomposition of the ingredients of the apocrine sweat from the first odorless secretion.

The decomposition products of the apocrine sweat, which contribute significantly to the body odor, in particular to the axillary body odor, can be divided into three classes: short-chain $C_4$-$C_{10}$ fatty acids, which may be linear, branched, saturated and unsaturated (for example, isovaleric acid, 3M2H) constitute the first class, short-chain linear or branched sulfanylalcohols constitute the second class, the third class of various steroid hormones and their metabolic products (for example, 5-alpha androstenol and 5-α androstenone).

Body odor can therefore be combated by avoiding the bacterial decomposition of the sweat, or by using perfume to cover the body odor. State-of-the-art antimicrobial substances are used to prevent the bacterial decomposition of the sweat. These reduce the number of sweat-decomposing bacteria on the skin by killing them or inhibiting the growth of these bacteria. Active substances are also known that reduce and/or prevent the formation of decomposition products by blocking bacterial enzymes. It is furthermore a commonly known fact that volatile decomposition products are absorbed by physical and/or chemical interaction, which avoids unpleasant body odor. Such state-of-the-art deodorants, however, have the disadvantage that the deodorizing effect usually only lasts for a period of from about 8 to about 20 hours. Although a prolonged deodorizing performance is possible by using acidic aluminum and/or aluminum zirconium salts. But these are viewed critically by consumers and can lead to skin irritation and undesirable textile stains. There is therefore a need for cosmetic agents, which are preferably free of aluminum and aluminum zirconium salts and also have a high deodorizing effect against body odor for from about 24 to about 48 hours after application.

The present disclosure was therefore based on the problem of preparing a cosmetic agent to reduce and/or prevent body odor, which has a long-lasting effect against body odor. These cosmetic products should also be cost-effective to produce and have a high storage stability.

BRIEF SUMMARY

Cosmetic agents and methods of using a mixture for cosmetic agents are provided herein. In an exemplary embodiment, a cosmetic agent, comprises, relative to the total weight thereof, a) at least one aromatic alcohol from Formula (I),

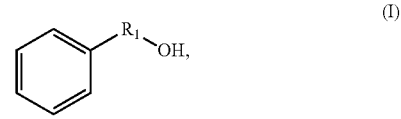

wherein $R_1$ stands for on linear $C_1$-$C_{10}$ alkylene group or a branched $C_1$-$C_{10}$ alkylene group, b) at least one menthyl compound from Formula (II)

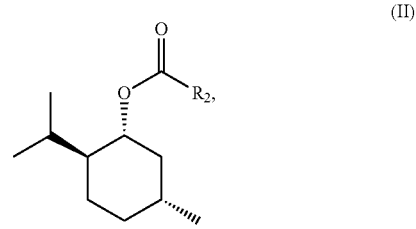

wherein $R_2$ denotes a $C_1$-$C_4$ alkyl group, and at least one deodorant ingredient.

In another exemplary embodiment, a method comprises using a mixture of a) at least one aromatic alcohol from Formula (I),

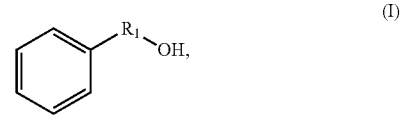

wherein $R_1$ stands for on linear $C_1$-$C_{10}$ alkylene group or a branched $C_1$-$C_{10}$ alkylene group, and b) at least one menthyl compound from Formula (II)

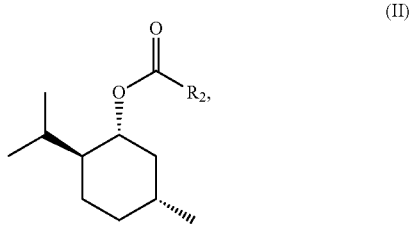
(II)

wherein
$R_2$ denotes a $C_1$-$C_4$ alkyl group,
to improve the odor-inhibiting effect of cosmetic agents over a period of from about 24 to about 48 hours.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Surprisingly, it has now been found that, by using a combination of at least one aromatic alcohol and at least one deodorizing menthyl compound, the effect of the preferred aluminum and aluminum zirconium salt-free cosmetic agents as contemplated herein can be extended significantly.

The first subject of this application is therefore a cosmetic agent containing—in relation to its total weight—
c) at least one aromatic alcohol from Formula (I).

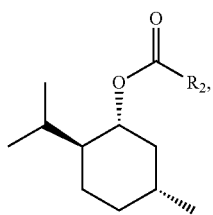
(I)

wherein
$R_1$ stands for on linear $C_1$-$C_{10}$ alkylene group or a branched $C_1$-$C_{10}$ alkylene group.
d) at least one menthyl compound from Formula (II)

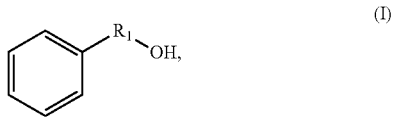
(II)

wherein
$R_2$ denotes a $C_1$-$C_4$ alkyl group and
e) at least one deodorant ingredient.

Compared to the use of the individual components, the use of a combination of at least one aromatic alcohol from Formula (I) and at least one menthyl compound from Formula (II) leads to a significant increase in the long-term effectiveness against unpleasant body odor. This makes it possible to achieve good deodorizing performance even from about 24 to about 48 hours after the application of the cosmetic agent as contemplated herein without using aluminum and aluminum zirconium salts. This mixture also has no unpleasant smell, which cannot be covered or only with extreme difficulty by the use of perfume, and can therefore easily be incorporated into existing formulations.

In the context of the present disclosure, the term 'deodorant active substance' is a compound which has anti-microbial, enzyme-inhibiting and/or absorbing properties. This also includes compounds that cover the unpleasant body odor resulting from the decomposition of sweat or that positively change the olfactory perception of body odor. The aromatic alcohol of Formula (I), the menthyl compound of Formula (II), as well as the ethanol used as a carrier are not, however, included in the deodorant agents as contemplated herein. The preferred deodorant agents are also not antiperspirant aluminum and/or aluminum zirconium salts. The preferred cosmetic agents of this present disclosure therefore contain 0 wt. % of antiperspirant aluminum and/or aluminum zirconium salts relative to the total weight of the cosmetic agents.

The indication wt. % in this case, unless otherwise specified, refers to the total weight of the cosmetic agents as contemplated herein, where the sum of all the agents as contemplated herein is 100 wt. %.

The cosmetic agent contains components (a) to (c) in a cosmetically acceptable carrier. This preferably contains at least one component selected from water, ethanol, a cosmetic oil that is liquid under normal conditions and mixtures thereof. The cosmetic oils that are liquid under normal conditions are not miscible with water and do not constitute fragrances or essential oils. In the sense of this application, "normal conditions" constitute a temperature of 20° C. and a pressure of 1013 hPa.

Preferred cosmetically acceptable carriers are aqueous, alcoholic or aqueous-alcoholic carriers preferably having at least about 10 wt. % water and or $C_1$-$C_4$ alcohol, relative to the total weight of the cosmetic agent.

It is particularly preferable that the cosmetically acceptable carrier contains water, particularly in a quantity that is preferably at least about 10 wt. %, more preferably at least about 20 wt %., most preferably at least about 30 wt. % water relative to the total weight of the cosmetic agent. Particularly preferred cosmetic products, in relation to their total weight, have a water content of from about 30 to about 98 wt. %, more preferably from about 30 to about 97 wt. %, most preferably from about 30 up to about 95 wt. %.

Alcoholic and/or water-alcoholic carriers preferably contain ethanol in a total of from about 25 to about 95 wt. %, more preferably from about 28 to about 92 wt. %, most preferably from about 30 to about 90 wt. %, relative to the total weight of the cosmetic agent.

Additional preferred carriers are water-free cosmetic carriers containing liquid cosmetic oils. These cosmetic oils can be selected from the group of (i) volatile non-silicone oils, in particular liquid paraffin oils and isoparaffin oils such as isodecan, isoundecan, isododecane, Isotridecan, Isotetradecan, Isopentadecan, isohexadecan and isoeicosan; (ii) non-volatile non-silicone oils, in particular the carboxylic acid esters and dicarboxylic acids of linear or branched $C_2$-$C_{10}$ alkanols, which can be esterified to the additive products of ethylene oxide and/or propylene oxide to mono- or polyhydric $C_3$-$C_{22}$ alkanols, which can if necessary be esterified, symmetrical, asymmetrical or cyclic esters of carbonic acid with fatty alcohols, esters of dimeric unsaturated $C_{12}$-22 fatty acids with monohydric, linear, branched and cyclic $C_2$-18 alkanols or $C_2$-6 alkanols, the benzoic acid esters of linear or branched $C_8$-22 alkanols such as benzoic acid $C_{12-15}$alkyl esters and benzoic acid isostearylesters, synthetic hydrocarbons, such as polyisobutene and polydecene, alicyclic hydrocarbons; and (iii) mixtures thereof.

The term "liquid cosmetic oil" refers to cosmetic oils as contemplated herein which have a vapor pressure of from about 2.66 Pa to about 40,000 Pa (from about 0.02 to about 300 mm Hg), preferably from about 10 to about 12,000 Pa (from about 0.1 to about 90 mm Hg), more preferably from about 13 to about 3,000 Pa (from about 0.1 to about 23 mm Hg), particularly from about 15 to about 500 Pa (from about 0.1 to about 4 mm Hg) at 20° C. and an environmental pressure of 1013 hPa. Furthermore, the term "non-liquid cosmetic oils" within the meaning of the present disclosure is understood to mean cosmetic oils that have a vapor pressure of less than 2.66 Pa (0.02 mm Hg) at 20° C. and an environmental pressure of 1,013 hPa.

As contemplated herein, use of mixtures of the above cosmetic oils, in particular, non-volatile and volatile cosmetic oils is more preferable, because this makes it possible to set parameters such as the skin feeling, visibility of residue and stability of the cosmetic agent as contemplated herein and, therefore, the agent can be better adapted to the needs of the consumer.

In the context of the present disclosure it is preferred if the cosmetic oil that is liquid at 20° C. and 1013 hPa is included in a total volume of from about 1.0 to about 98 wt. %, preferably from about 25 to about 80 wt. %, more preferably from about 60 to about 95 wt. %, particularly preferred from about 65 to about 92 wt. %, more particularly preferred from about 70 to about 90 wt. %, based on the total weight of the cosmetic agent.

As the first essential component a) the cosmetic agent as contemplated herein contains at least one aromatic alcohol from Formula (I).

Preferred as contemplated herein are aromatic alcohols from Formula (I), in which the radical $R_1$ denotes certain groups. Advantageous cosmetic products as contemplated herein are characterized by the fact that, in Formula (I) the radical $R_1$ denotes *—$CH_2$—$CH_2$—$C(CH_3)_2$—**. The binding of the radical $R_1$ to the benzene is denoted by the symbol *, and the binding of the radical $R_1$ to the OH group by the symbol **. The use of these aromatic alcohols, in particular 2-methyl-4-phenyl-2-butanol ($R_1$=*—$CH_2$—$CH_2$—$C(CH_3)_2$—**), in a compound with at least one menthyl compound from Formula (II) leads to an excellent deodorizing effect of the cosmetic agent as contemplated herein even from about 24 to about 48 hours after application.

As the second essential component b) the cosmetic agent as contemplated herein contains at least one menthyl compound from Formula (I). In the context of the present disclosure, however, it has been proven to be beneficial if certain menthyl compounds are used. It is therefore preferable if, in Formula (II), the radical $R_2$ denotes *—$CH_3$. The binding of the radical $R_3$ to the carbonyl group is denoted by the symbol *. The use of such menthyl compounds from Formula (II), and in particular menthyl acetate ($R_2$=*—$CH_3$), in conjunction with the at least one aromatic alcohol from Formula (I), and in particular 2-Methyl-4-phenyl-2-butanol ($R_1$=*—$CH_2$—$CH_2$—$C(CH_3)_2$—**) leads to an extension of the deodorizing performance of the cosmetic agent as contemplated herein. This makes it possible to avoid using skin-irritating aluminum and/or aluminum zirconium salts, which are currently used to extend the deodorizing effect. In addition, the risk of allergies can be reduced because the low inherent odor of these compounds, as well as their excellent and long-lasting deodorizing effect, means that additional allergenic fragrance components to cover the inherent smell or to obtain an adequate deodorant performance are not required or only in very small quantities.

The aromatic alcohol of Formula (I), and in particular 2-Methyl-4-phenyl-2-butanol ($R_1$=*—$CH_2$—$CH_2$—$C(CH_3)_2$—**), is preferably contained in certain total quantities in the cosmetic agent as contemplated herein. It is therefore preferred as contemplated herein as if at least one aromatic alcohol of Formula (I), and in particular 2-Methyl-4-phenyl-2-butanol, is contained in a total amount of from about 0.010 to about 2.0 wt. %, more preferably from about 0.030 to about 1.0 wt. %, preferred from about 0.040 to about 0.70 wt. %, more particularly preferred from about 0.050 to about 0.50 wt. %, respectively in relation to the total weight of the cosmetic agent. If a mixture of different aromatic alcohols of Formula (I) is used, these quantity specifications relate to the total quantity of the mixture of alcohols of Formula (I). The long-lasting effect in terms of odor neutralization is already obtained in very small quantities of the aromatic alcohol of Formula (I), and in particular of 2-Methyl-4-phenyl-2-butanol ($R_1$=*—$CH_2$—$CH_2$—$C(CH_3)_2$—**). Because of the low inherent smell of these alcohols in the defined quantity ranges, use of additional allergenic perfume components to cover the inherent smell, or to obtain adequate deodorizing performance is not absolutely necessary. Even without using aluminum and/or aluminum zirconium salts, which are currently used to extend the deodorizing effect, the cosmetic agent as contemplated herein also has an outstanding deodorizing effect even from about 24 to about 48 hours after application.

The menthyl compound of Formula (II), in particular menthyl acetate ($R_2$=*—$CH_3$), is preferably contained in certain total quantities in the cosmetic agent as contemplated herein. It is therefore preferred as contemplated herein if at least one menthyl compound of Formula (II), in particular menthyl acetate, is contained in a total amount of 0.01 to 1.0 wt. %, more preferably from about 0.02 to about 0.80 wt. %, preferred from about 0.03 to about 0.60 wt. %, more particularly preferred from about 0.05 to about 0.50 wt. %, respectively in relation to the total weight of the cosmetic agent. If a mixture of different menthyl compounds of Formula (II) is used, these quantity specifications relate to the total quantity of the mixture of menthyl compounds of Formula (II). The long-lasting deodorizing performance is already obtained in very small quantities of the menthyl compound in Formula (II), and in particular of menthyl acetate ($R_2$=*—$CH_3$). Because of the low inherent smell of menthyl compounds in the defined quantity ranges, usage of additional allergenic perfume components is not absolutely necessary. Even without using aluminum and/or aluminum zirconium salts, which are currently used to extend the deodorizing effect, the cosmetic agent as contemplated herein also has an outstanding deodorizing effect even 24 to 48 hours after application.

In the context of the present disclosure, it has proven to be particularly beneficial when certain weight ratios of the aromatic alcohol in Formula (I), in particular 2-Methyl-4-phenyl-2-butanol ($R_1$=*—$CH_2$—$CH_2$—$C(CH_3)_2$—**), are used with at least one menthyl compound of Formula (II), in particular menthyl acetate ($R_2$=*—$CH_3$). It is therefore preferred as contemplated herein if the cosmetic agent has a weight ratio of at least one aromatic alcohol of Formula (I), in particular 2-Methyl-4-phenyl-2-butanol to at least one menthyl compound of Formula (II), in particular, menthyl acetate, of from about 75:1 to about 1:300, preferably of from about 16:1 to about 1:16, preferred of from about 6:1 to about 1:12, more preferably of from about 2:1 to about 1:12. The use of the previously mentioned weight ratios leads to particularly long-lasting neutralization of unpleasant body odor. In addition, mixtures of the claimed alcohols and menthyl compounds in the previously mentioned weight ratios have neither an allergenic potential nor a strong inherent smell.

As the third essential component c) the cosmetic agent as contemplated herein contains at least one active deodorant substance.

In the context of the present disclosure, specific active deodorant agents are preferred. It is therefore preferred as contemplated herein if the active deodorant agent is selected from the group of (i) arylsulfatase inhibitors, ß-glucuronidase inhibitors, aminoacylase inhibitors, esterase inhibitors, lipase inhibitors and lipoxigenase inhibitors; (ii) α-mono alkyl glycerol ethers with a branched or linear saturated or unsaturated, where appropriate hydroxylated $C_6$-$C_{22}$-alkyl radical, in particular, α-(2-Ethylhexyl)glycerin ether, (iii) Alcohols, in particular, phenoxyethanol, benzylheptanol, 1,2-hexandiol, 1,2-octandiol, 1,2-decandiol, tropolon and butyloctane acid; (iv) germ-inhibiting perfume oils; (v) prebiotic substances; (vi) trialkyl citric acid esters, in particular, triethyl citrate; (vii) active ingredients, that reduce the number of skin germs involved in the development of odors from the group of staphylococci, *corynebacterium, anaerococcus* and micrococci or inhibit their growth; (viii) zinc and silver compounds, in particular, zinc phenol sulfonate, zinc ricinoleate, Bichloride(-1)-octahydroxy pentazinc, zinc citrate and silver lactate; (ix) organic halogen compounds, in particular, triclosan, chlorhexidine and chlorhexidingluconate; (x) benzalkonium halogenides, in particular, benzalkonium chloride and benzethonium chloride; (xi) quaternary ammonium compounds, in particular, cetylpyridiniumchloride; (xii) carbonates, phosphates and sulfates with an antimicrobial effect, in particular, sodium bicarbonate, Cocamidopropyl PG-Dimonium Chloride Phosphate, disodium pyrophosphate and Soya Morpholinium Ethosulfate; (xiii) Lantibiotics; (xiv) Bispyridines, in particular, octenidine; (xv) acids with an antimicrobial effect, in particular, Caprylhydroxam acid, Carnesol acid and tartaric acid; (xvi) Polyglycerine ester; (xvii) Sorbitan esters and Lactones, in particular, sorbitan caprylate and Glucono-1,5-lacton; (xviii) and mixtures thereof, in particular, Phenoxyethanol and/or triethyl citrate. The long-lasting deodorizing effect achieved by mixing aromatic alcohol from Formula (I), in particular, 2-Methyl-4-phenyl-2-butanol ($R_1$=*—$CH_2$—$CH_2$—C($CH_3$)$_2$—**), and menthyl compounds from Formula (II), in particular, menthyl acetate ($R_2$=*—$CH_3$), can be further improved if triethyl citrate and/or phenoxyethanol is used as an active deodorant agent.

In the context of the present disclosure, it can be preferable to use at least one active deodorant agent, in particular triethyl citrate and/or phenoxyethanol, in a specific total quantity. Preferred embodiments of the cosmetic agent as contemplated herein are therefore characterized in that they contain at least one of the active deodorant agents, in particular triethyl citrate and/or phenoxyethanol, in a total amount of from about 0.0001 to about 15 wt. %, preferably from about 0.001 to about 12 wt. %, preferred from about 0.01 to about 10 wt. %, in particular from about 0.5 to about 8.0 wt. %, respectively in relation to the total weight of the cosmetic agent. The use of at least one active deodorant agent, in particular, triethyl citrate and/or phenoxyethanol, in the previously mentioned total quantities leads to a further improvement of the long-lasting effect achieved by combining aromatic alcohol from Formula (I), and in particular of 2-Methyl-4-phenyl-2-butanol ($R_1$=*—$CH_2$—$CH_2$—C($CH_3$)$_2$—**), and menthyl compound from Formula (II), in particular, menthyl acetate ($R_2$=*—$CH_3$).

The cosmetic agents as contemplated herein are preferably deodorant compositions. It is therefore advantageous if the cosmetic agent contains antiperspirant compounds, in particular, aluminum and aluminum zirconium salts, in a total amount of 0 wt. % in relation to the total weight of the cosmetic agent. In the context of the present disclosure, antiperspirant compounds are understood to mean compounds that are capable of reducing and/or avoiding the production of sweat. It is particularly preferable that the cosmetic agent as contemplated herein does not contain any antiperspirant salts of aluminum and/or aluminum-zirconium. Because these salts irritate the skin due to their low pH-value and may also facilitate the formation of textile stains, the cosmetic agents of this embodiment have good skin compatibility as well as minimal textile soiling.

In addition to the previously mentioned mandatory components (a) to (c), the cosmetic agents according to this present disclosure contain additional ingredients. These ingredients are preferably selected from the group of (i) fragrances; (ii) emulsifiers and/or surfactants; (iii) thickening agents; (iv) chelating agents; and (v) mixtures thereof.

Preferred embodiments of the present disclosure additionally contain at least one fragrance. As contemplated herein, these are understood as substances with a molecular weight of from about 74 to about 300 g/mol containing at least one osmophore group in the molecule and a smell and/or taste, i.e. they are able to excite the receptors of the hair cells of the olfactory system. Osmophore groups are covalently bound to the molecule structure groups in the form of hydroxyl groups, formyl groups, oxo groups, alkoxycarbonyl groups, nitrile groups, nitro groups, azide groups, etc. In this context, perfume oils liquid at 20° C. and 1013 hPa, perfumes or perfume oil constituents are also included in the term fragrance. In the context of the present disclosure, usable fragrances include, for example (i) esters, in particular benzyl acetate, phenoxyethyl isobutyrate, p-tert-butyl cyclohexyl acetate, linalyl acetate, dimethyl benzyl carbinyl acetate (DMBCA), phenylethyl acetate, benzyl acetate, ethyl methylphenylglycinate, allyl cyclohexyl propionate, styrallyl propionate, benzyl salicylate, cyclohexyl salicylate, floramat, Melusat and Jasmecyclat; (ii) ether, particularly benzyl ethyl ether and Ambroxan; (iii) aldehydes, in particular linear alkanes with 8 to 18 carbon atoms, citral, citronellal, citronellyl oxyacetaldehyde, cyclamen aldehyde, lilial and bourgeonal; (iv) ketones, particularly Jonone, alpha-Isomethyl ionone and methyl cedryl ketone; (v) alcohols, particularly anethole, citronellol, eugenol, geraniol and linalool, phenethyl alcohol and terpineol; (vi) hydrocarbons, in particular terpenes such as limonene and pinene; and (vii) mixtures thereof. Preferably, mixtures of different fragrances are used that, together, produce a pleasant scent.

Particularly appealing smelling cosmetic agents as contemplated herein are obtained if the fragrance is present in a total amount of from about 0.00001 to about 10 wt. %, preferably from about 0.001 to about 9.0 wt. %, preferred from about 0.01 to about 8.0 wt. %, more preferably from about 0.5 to about 7.0 wt. %, in particular from about 1.0 to about 6.0 wt. %, in relation to of the cosmetic agent.

As contemplated herein, suitable surfactants are preferably selected from anionic, cationic, non-ionic, amphoteric, particularly ampholytic and zwitterionic emulsifiers and surfactants. Surfactants are amphiphilic (bifunctional) compounds, which include at least one hydrophobic and at least one hydrophilic molecular part. The hydrophobic radical is preferably a hydrocarbon chain with 8 to 28 carbon atoms, which can be saturated or unsaturated, linear or branched. It is especially preferable if this $C_8$-$C_{28}$ alkyl chain is linear.

Anionic surfactants are understood to mean exclusively anionic charges; they contain e.g. carboxyl, sulfonic acid groups or sulfate groups. Particularly preferred anionic surfactants are alkyl sulfates, alkyl ether sulfates, acyl glutamates and $C_{8-24}$ carboxylic acids and their salts, the so-called soaps.

Cationic surfactants are understood to mean exclusively cationic charges; they contain e.g. quarternary ammonium groups. Preferably cationic surfactants of the following types: quaternary ammonium compounds, esterquats, and amide amines. Preferred quaternary ammonium compounds are ammonium halides, as well as those known under the INCI names Quaternium-27 and Quaternium-83 imidazolium compounds. As contemplated herein, the quaternized protein hydrolysates can also be used. Preferred esterquats are quaternized ester salts of fatty acids with triethanolamine, quaternated ester salts of fatty acids with diethanolalkyl amines and quaternated ester salts of fatty acids with 1,2-dihydroxypropyldialkylamines.

The amphoteric surfactants are divided into ampholytic surfactants and zwitterionic surfactants. Ampholytic surfactants are surface active compounds that contain both acid (for example, —COOH or —$SO_3H$ groups) and also alkaline hydrophilic groups (for example, amino groups) and have acidic or alkaline behavior depending on the condition. Zwitterionic surfactants are specialist surfactants that carry both a negative and a positive charge in the same molecule. Examples of preferred zwitterionic surfactants are betaines, the N-alkyl-N, N-dimethylammoniumglycinates, N-Acylaminopropyl-N, N-dimethylammoniumglycinate and the 2-alkyl-3-carboxymethyl-3-hydroxyethyl-imidazolines,
each having 8 to 24 carbon atoms in the alkyl group. Examples of preferred ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkyl sarcosines, 2-alkylaminopropionic acids and alkylaminoacetic acids having in each case about 8 to 24 carbon atoms in the alkyl group.

Particularly preferred cosmetic agents as contemplated herein contain at least one non-ionic surfactant. Such surfactants are preferably selected from the group including of alkoxylated $C_8$-$C_{24}$ alkanols with from about 2 to about 30 mol alkylene oxide per mol of alkanol, alkoxylated $C_8$-$C_{24}$ carboxylic acids with from about 2 to about 30 mol alkylene oxide per mol of carboxylic acid, silicone copolyols with ethylene oxide units or with ethylene oxide and propylene oxide units, alkyl mono- and oligoglycosides containing 8 to 22 carbon atoms in the alkyl radical and ethoxylated analogs thereof, ethoxylated sterols, partial esters of polyglycerols having from about 2 to about 10 glycerol units and from about 1 to about 4 saturated or unsaturated, linear or branched $C_8$-$C_{22}$ fatty acid residues and mixtures thereof. In order to ensure sufficient stability of the cosmetic agent as contemplated herein, these nonionic surfactants are used in certain total quantities. Preferred cosmetic compositions are therefore characterized by the fact that they contain at least one nonionic surfactant in a total quantity of from about 0.5 to about 10 wt.-%, in particular from about 0.5 to about 5.0 wt.-%, based on the total weight of the cosmetic agent. Particularly preferred emulsifiers are ethoxylated $C_8$-$C_{24}$ alkanols with from about 2 to about 30 mol of ethylene oxide per mol of alkanol and propoxylated $C_8$-$C_{24}$ alkanols with from about 10 to about 20 mol of propylene oxide per mol of alkanol. In this context, stearyl ether with from about 2 to about 21 mol ethylene oxide, stearyl ether with 15 mol propylene oxide, hydrogenated castor oil with from about 30 to about 50 mol ethylene oxide and cetearyl ether with from about 12 to about 30 mol ethylene oxide are particularly preferred.

Preferably, the cosmetic agents as contemplated herein are formulated as free-flowing preparations. The cosmetic agents must be formulated in such a manner that they can be readily applied and distributed at the place of use and are easy to dispense from the packaging. It is therefore preferred in the context of the present disclosure if the cosmetic agents as contemplated herein additionally contain at least one thickening agent selected from the group of cellulose ethers, xanthan gum, *sclerotium* gum, succinoglucanen, guar gums, locust bean gum, nonionic hydroxyalkyl guar derivatives and locust bean gum derivatives, pectins, agar, carrageenan, tragacanth, gum arabic, karaya gum, tara gum, gellan, gelatin, casein, hydroxyalkyl celluloses, propylene glycol alginate, alginic acids and salts thereof, polyvinyl pyrrolidones, polyvinyl alcohols, polyacrylamides, hydroxypropylated starch phosphates and oxidized starch succinates acrylic acid-acrylate copolymers, acrylic acid-acrylamide copolymers, acrylic acid-vinylpyrrolidone copolymers, acrylic acid-vinyl formamide copolymers, and polyacrylates, in a total amount of from about 0.01 to about 2.0 wt.-%, in particular from about 0.1 to about 0.5.-%, based on the total weight of the cosmetic agent. Preferred thickening agents are selected from cellulose ethers, especially from hydroxyalkylcelluloses, in particular hydroxy propylcellulose, hydroxypropyl methylcellulose, hydroxyethyl cellulose, carboxymethyl cellulose, cetyl hydroxyethyl cellulose, hydroxybutyl methyl cellulose and methyl hydroxyethyl cellulose, and mixtures thereof. Hydroxyethyl cellulose is used as a preferred thickening agent.

To increase the deodorizing effect, it may be advantageous to add at least one chelating agent to the cosmetic agent as contemplated herein. Preferred cosmetic agents are therefore characterized by the fact that they also contain at least one chelating agent selected from the group of ethylenediaminetetraacetic acid (EDTA) and its salts, in a total amount of from about 0.01 to about 0.5 wt. %, in particular from about 0.05 to about 0.2 wt. %, based on the total weight of the cosmetic agent.

The following tables list particularly preferred embodiments of AF 1 to AF 60 of the cosmetic agent as contemplated herein (all figures in wt. %). These agents preferably contain 0 wt. %, based on the total weight of the cosmetic agent, of antiperspirant compounds, in particular salts of aluminum and/or aluminum zirconium.

|  | AF 1 | AF 2 | AF 3 | AF 4 |
|---|---|---|---|---|
| Aromatic alcohol from Formula (I) | 0.010-2.0 | 0.030-1.0 | 0.040-0.70 | 0.050-0.50 |
| Menthyl compound from Formula (II) | 0.01-1.0 | 0.02-0.80 | 0.03-0.60 | 0.05-0.50 |

|  |  |  |  |  |
|---|---|---|---|---|
| Deodorant agent | 0.0001-15 | 0.001-12 | 0.01-10 | 0.5-8.0 |
| Cosmetic carrier | ad 100 | ad 100 | ad 100 | ad 100 |

|  | AF 5 | AF 6 | AF 7 | AF 8 |
|---|---|---|---|---|
| Aromatic alcohol from Formula (I) [1] | 0.010-2.0 | 0.030-1.0 | 0.040-0.70 | 0.050-0.50 |
| Menthyl compound from Formula (II) | 0.01-1.0 | 0.02-0.80 | 0.03-0.60 | 0.05-0.50 |
| Deodorant agent | 0.0001-15 | 0.001-12 | 0.01-10 | 0.5-8.0 |
| Cosmetic carrier | ad 100 | ad 100 | ad 100 | ad 100 |

|  | AF 9 | AF 10 | AF 11 | AF 12 |
|---|---|---|---|---|
| Aromatic alcohol from Formula (I) | 0.010-2.0 | 0.030-1.0 | 0.040-0.70 | 0.050-0.50 |
| Menthyl compound from Formula (II) [2] | 0.01-1.0 | 0.02-0.80 | 0.03-0.60 | 0.05-0.50 |
| Deodorant agent | 0.0001-15 | 0.001-12 | 0.01-10 | 0.5-8.0 |
| Cosmetic carrier | ad 100 | ad 100 | ad 100 | ad 100 |

|  | AF 13 | AF 14 | AF 15 | AF 16 |
|---|---|---|---|---|
| Aromatic alcohol from Formula (I) | 0.010-2.0 | 0.030-1.0 | 0.040-0.70 | 0.050-0.50 |
| Menthyl compound from Formula (II) | 0.01-1.0 | 0.02-0.80 | 0.03-0.60 | 0.05-0.50 |
| Deodorant agent [3] | 0.0001-15 | 0.001-12 | 0.01-10 | 0.5-8.0 |
| Cosmetic carrier | ad 100 | ad 100 | ad 100 | ad 100 |

|  | AF 17 | AF 18 | AF 19 | AF 20 |
|---|---|---|---|---|
| Aromatic alcohol from Formula (I) [1] | 0.010-2.0 | 0.030-1.0 | 0.040-0.70 | 0.050-0.50 |
| Menthyl compound from Formula (II) [2] | 0.01-1.0 | 0.02-0.80 | 0.03-0.60 | 0.05-0.50 |
| Deodorant agent | 0.0001-15 | 0.001-12 | 0.01-10 | 0.5-8.0 |
| Cosmetic carrier | ad 100 | ad 100 | ad 100 | ad 100 |

|  | AF 21 | AF 22 | AF 23 | AF 24 |
|---|---|---|---|---|
| Aromatic alcohol from Formula (I) [1] | 0.010-2.0 | 0.030-1.0 | 0.040-0.70 | 0.050-0.50 |
| Menthyl compound from Formula (II) | 0.01-1.0 | 0.02-0.80 | 0.03-0.60 | 0.05-0.50 |
| Deodorant agent [3] | 0.0001-15 | 0.001-12 | 0.01-10 | 0.5-8.0 |
| Cosmetic carrier | ad 100 | ad 100 | ad 100 | ad 100 |

|  | AF 25 | AF 26 | AF 27 | AF 28 |
|---|---|---|---|---|
| Aromatic alcohol from Formula (I) | 0.010-2.0 | 0.030-1.0 | 0.040-0.70 | 0.050-0.50 |
| Menthyl compound from Formula (II) [2] | 0.01-1.0 | 0.02-0.80 | 0.03-0.60 | 0.05-0.50 |
| Deodorant agent [3] | 0.0001-15 | 0.001-12 | 0.01-10 | 0.5-8.0 |
| Cosmetic carrier | ad 100 | ad 100 | ad 100 | ad 100 |

|  | AF 29 | AF 30 | AF 31 | AF 32 |
|---|---|---|---|---|
| Aromatic alcohol from Formula (I) [1] | 0.010-2.0 | 0.030-1.0 | 0.040-0.70 | 0.050-0.50 |
| Menthyl compound from Formula (II) [2] | 0.01-1.0 | 0.02-0.80 | 0.03-0.60 | 0.05-0.50 |
| Deodorant agent [3] | 0.0001-15 | 0.001-12 | 0.01-10 | 0.5-8.0 |
| Cosmetic carrier | ad 100 | ad 100 | ad 100 | ad 100 |

|  | AF 33 | AF 34 | AF 35 | AF 36 |
|---|---|---|---|---|
| Aromatic alcohol from Formula (I) [1] | 0.010-2.0 | 0.030-1.0 | 0.040-0.70 | 0.050-0.50 |
| Menthyl compound from Formula (II) [2] | 0.01-1.0 | 0.02-0.80 | 0.03-0.60 | 0.05-0.50 |
| Deodorant agent [3] | 0.0001-15 | 0.001-12 | 0.01-10 | 0.5-8.0 |
| Non-ionic surfactant [4] | 0.5-10 | 0.5-8.0 | 0.5-6.0 | 0.5-5.0 |
| Cosmetic carrier | ad 100 | ad 100 | ad 100 | ad 100 |

|  | AF 37 | AF 38 | AF 39 | AF 40 |
|---|---|---|---|---|
| Aromatic alcohol from Formula (I) [1] | 0.010-2.0 | 0.030-1.0 | 0.040-0.70 | 0.050-0.50 |
| Menthyl compound from Formula (II) [2] | 0.01-1.0 | 0.02-0.80 | 0.03-0.60 | 0.05-0.50 |
| Deodorant agent [3] | 0.0001-15 | 0.001-12 | 0.01-10 | 0.5-8.0 |
| Thickener [5] | 0.1-2.0 | 0.1-1.5 | 0.1-1.0 | 0.1-0.5 |
| Cosmetic carrier | ad 100 | ad 100 | ad 100 | ad 100 |

|  | AF 41 | AF 42 | AF 43 | AF 44 |
|---|---|---|---|---|
| Aromatic alcohol from Formula (I) [1] | 0.010-2.0 | 0.030-1.0 | 0.040-0.70 | 0.050-0.50 |
| Menthyl compound from Formula (II) [2] | 0.01-1.0 | 0.02-0.80 | 0.03-0.60 | 0.05-0.50 |
| Deodorant agent [3] | 0.0001-15 | 0.001-12 | 0.01-10 | 0.5-8.0 |
| Chelating agents [6] | 0.01-0.5 | 0.02-0.4 | 0.03-0.3 | 0.05-0.2 |
| Cosmetic carrier | ad 100 | ad 100 | ad 100 | ad 100 |

|  | AF 45 | AF 46 | AF 47 | AF 48 |
|---|---|---|---|---|
| Aromatic alcohol from Formula (I) [1] | 0.010-2.0 | 0.030-1.0 | 0.040-0.70 | 0.050-0.50 |
| Menthyl compound from Formula (II) [2] | 0.01-1.0 | 0.02-0.80 | 0.03-0.60 | 0.05-0.50 |
| Deodorant agent [3] | 0.0001-15 | 0.001-12 | 0.01-10 | 0.5-8.0 |
| Non-ionic surfactant [4] | 0.5-10 | 0.5-8.0 | 0.5-6.0 | 0.5-5.0 |
| Thickener [5] | 0.1-2.0 | 0.1-1.5 | 0.1-1.0 | 0.1-0.5 |
| Cosmetic carrier | ad 100 | ad 100 | ad 100 | ad 100 |

|  | AF 49 | AF 50 | AF 51 | AF 52 |
|---|---|---|---|---|
| Aromatic alcohol from Formula (I) [1] | 0.010-2.0 | 0.030-1.0 | 0.040-0.70 | 0.050-0.50 |
| Menthyl compound from Formula (II) [2] | 0.01-1.0 | 0.02-0.80 | 0.03-0.60 | 0.05-0.50 |
| Deodorant agent [3] | 0.0001-15 | 0.001-12 | 0.01-10 | 0.5-8.0 |
| Non-ionic surfactant [4] | 0.5-10 | 0.5-8.0 | 0.5-6.0 | 0.5-5.0 |
| Chelating agents [6] | 0.01-0.5 | 0.02-0.4 | 0.03-0.3 | 0.05-0.2 |
| Cosmetic carrier | ad 100 | ad 100 | ad 100 | ad 100 |

|  | AF 53 | AF 54 | AF 55 | AF 56 |
|---|---|---|---|---|
| Aromatic alcohol from Formula (I) [1] | 0.010-2.0 | 0.030-1.0 | 0.040-0.70 | 0.050-0.50 |
| Menthyl compound from Formula (II) [2] | 0.01-1.0 | 0.02-0.80 | 0.03-0.60 | 0.05-0.50 |
| Deodorant agent [3] | 0.0001-15 | 0.001-12 | 0.01-10 | 0.5-8.0 |
| Thickener [5] | 0.1-2.0 | 0.1-1.5 | 0.1-1.0 | 0.1-0.5 |
| Chelating agents [6] | 0.01-0.5 | 0.02-0.4 | 0.03-0.3 | 0.05-0.2 |
| Cosmetic carrier | ad 100 | ad 100 | ad 100 | ad 100 |

|  | AF 57 | AF 58 | AF 59 | AF 60 |
|---|---|---|---|---|
| Aromatic alcohol from Formula (I) [1] | 0.010-2.0 | 0.030-1.0 | 0.040-0.70 | 0.050-0.50 |
| Menthyl compound from Formula (II) [2] | 0.01-1.0 | 0.02-0.80 | 0.03-0.60 | 0.05-0.50 |
| Deodorant agent [3] | 0.0001-15 | 0.001-12 | 0.01-10 | 0.5-8.0 |
| Non-ionic surfactant [4] | 0.5-10 | 0.5-8.0 | 0.5-6.0 | 0.5-5.0 |
| Thickener [5] | 0.1-2.0 | 0.1-1.5 | 0.1-1.0 | 0.1-0.5 |
| Chelating agents [6] | 0.01-0.5 | 0.02-0.4 | 0.03-0.3 | 0.05-0.2 |
| Cosmetic carrier | ad 100 | ad 100 | ad 100 | ad 100 |

[1] Radical $R_1$ denotes *—$CH_2$—$CH_2$—$C(CH_3)_2$—**.
[2] Radical $R_2$ denotes *—$CH_3$.
[3] Triethyl citrate and/or phenoxyethanol,
[4] selected from the group of stearyl ether with from about 2 to about 21 mol ethylene oxide, stearyl ether with 15 mol propylene oxide, hydrogenated castor oil with from about 30 to about 50 mol ethylene oxide and cetearyl ether with from about 12 to about 30 mol ethylene oxide.
[5] Hydroxyethyl cellulose,
[6] Sodium salts of ethylenediaminetetraacetic acid (EDTA)

The above embodiments from about 1 to about 60 of the cosmetic agent as contemplated herein, by using a combination of one aromatic alcohol from Formula (I), in particular 2-Methyl-4-phenyl-2-butanol ($R_1$=*—$CH_2$—$CH_2$—$C(CH_3)_2$—**), with a menthyl compound from Formula (II), in particular, menthyl acetate ($R_2$=*—$CH_3$), achieved a longer-lasting deodorizing effect in comparison to the use of the individual components. These compounds also do not have an unpleasant inherent smell in the required total quantities. Due to the presence of antiperspirant aluminum and/or aluminum zirconium salts, these embodiments are particularly skin-friendly and do not result in unwanted textile soiling.

Formulation of the agent as contemplated herein in a specific dosage form, such as a roll-on, stick or gel is preferentially based on the requirements of the intended use. Therefore, depending on the intended use, the agents as contemplated herein can be produced in a solid, semi-solid, liquid, dispersed, emulsified, suspended, gel-like, multi-phase or powder form. For the purposes of the present disclosure, the term "liquid" also encompasses any type of solid-state dispersions in liquids. Furthermore, in the context of the present disclosure, multi-phase agents as contemplated herein are understood to mean agents that have at least two different phases with a phase separation in which the phases may be arranged horizontally, in other words, one above the other, or vertically, that is to say, next to one another. The agent can be applied, for example, as a solid stick, soft solid, creme, roll-on, dibenzylidene alditol-based gel, loose or compact powder.

Creme, gel, paste and fluid agents as contemplated herein may, for example, be packed in pump, spray or squeeze dispensers, in particular, also in multi-chamber pump, spray or squeeze dispensers. The packaging can be opaque but also transparent or translucent and does not contain any propellants.

The application of the agent as contemplated herein is preferably carried out using a spray device with at least one propellant and the cosmetic agent as contemplated herein in a container. A second subject matter of the present disclosure is therefore a cosmetic product comprising
a) at least one cosmetic agent as contemplated herein
b) at least one propellant.

Suitable containers for such cosmetic products are, for example, cylindrical vessels made of metal (aluminum, tinplate, preferred capacity maximum 1000 ml), protected or non-splintering glass or plastic (preferred capacity maximum 220 ml) or splintering glass or plastic (capacity preferably from about 50 to about 400 ml). These containers also contain a valve that is used to dispense the cosmetic agent as contemplated herein in the form of a mist, fumes, foam, powder, paste or a liquid jet.

The cosmetic agent refers to the agents described under the first subject matter of the present disclosure. Therefore, all embodiments of the cosmetic agents of the first subject matter of the present disclosure also apply mutatis mutandis to the preferred embodiments of the cosmetic product. The cosmetic product as contemplated herein preferably contains the cosmetic agents in certain total quantities. Advantageous embodiments of the subject matter of the present disclosure are therefore characterized in that the cosmetic product contains at least one cosmetic agent in a total quantity of from about 5.0 to about 50 wt. %, preferably from about 5.0 to about 25 wt. %, more preferably from about 8.0 to about 20 wt. %, in particular from about 10 to about 15 wt. %, based on the total weight of the cosmetic product. The total weight of the cosmetic product is therefore the sum of the weight of the cosmetic agent and the propellant. On the other hand, the weight of the packaging of the cosmetic product, in particular of the container with a valve, is not taken into account.

In the context of the subject matter of the present disclosure it has proved advantageous when certain compounds are used as propellants. It is therefore preferable if at least one propellant is selected from the group of propane, propene, n-butane, isobutane, isobutene, n-pentane, pentene, isopentane, isopentene, methane, ethane, dimethyl ether, nitrogen, air, oxygen, nitrous oxide, 1,1,1,3-tetrafluoroethane, heptafluoro-n-propane, perfluoroethane, monochlorodifluormethane, 1,1-difluorethane and tetrafluoropropenes, and mixtures thereof. Particularly preferred propellants are propane, n-butane, isobutane and mixtures thereof, in particular a mixture of propane and n-butane in a weight ratio of 15:85.

To ensure sufficient sprayability of the cosmetic agent as contemplated herein, it is advantageous if the cosmetic product contains at least one propellant in a certain total quantity. Therefore, preferred embodiments are characterized in that they contain at least one propellant in a total quantity of from about 10 to about 95 wt. %, preferably from about 60 to about 95 wt. %, more preferably from about 70 to about 95 wt. %, and most preferably from about 75 to about 95 wt. %, relative to the total weight of the cosmetic product. The total weight of the cosmetic product is therefore the sum of the weight of the cosmetic agent and the propellant. On the other hand, the weight of the packaging of the cosmetic product, in particular of the container with a valve, is not taken into account.

Especially preferred embodiments K1 to K12 of the cosmetic product as contemplated herein (all data in wt. %) are described below.

|  | K 1 | K 2 | K 3 | K 4 |
|---|---|---|---|---|
| Cosmetic agent [1] | 5.0-50 | 5.0-25 | 8.0-20 | 10-15 |
| Propellant | Ad 100 | Ad 100 | Ad 100 | Ad 100 |
|  | K 5 | K 6 | K 7 | K 8 |
| Cosmetic agent [1] | 5.0-50 | 5.0-25 | 8.0-20 | 10-15 |
| Propellant [2] | Ad 100 | Ad 100 | Ad 100 | Ad 100 |
|  | K 9 | K 10 | K 11 | K 12 |
| Cosmetic agent [1] | 5.0-50 | 5.0-25 | 8.0-20 | 10-15 |
| Propellant (E) [3] | Ad 100 | Ad 100 | Ad 100 | Ad 100 |

[1] selected from one of the particularly preferred embodiments AF1 to AF60 referred to in the first subject of the present disclosure,
[2] selected from the group of propane, propene, n-butane, isobutane, isobutene, n-pentane, pentene, isopentane, isopentene, methane, ethane, dimethyl ether, nitrogen, air, oxygen, nitrous oxide, 1,1,1,3-tetrafluoroethane, heptafluoro-n-propane, perfluoroethane, monochlorodifluormethane, 1,1-difluorethane and tetrafluoropropenes, and mixtures thereof.
[3] selected from propane, n-butane, iso-butane and mixtures thereof The aforementioned cosmetic products K1-K12 have good sprayability. Furthermore, these products do not cause premature clogging of the valves and can be completely sprayed. These products also have no corrosive properties and a high level of storage stability. The use of these products leads to an outstanding deodorizing performance even in the absence of allergenic deodorizing perfume components.

With respect to further preferred embodiments of the cosmetic agent as contemplated herein, the statements made about the anhydrous preparation as contemplated herein apply mutatis mutandis.

A third subject matter of the present disclosure relates to the use of the cosmetic agent as contemplated herein or the cosmetic product as contemplated herein for the reduction of body odor caused by perspiration.

Because of the combination of special aromatic alcohols of Formula (I) with special menthyl compounds from Formula (II), the use of the cosmetic agent as contemplated herein or the cosmetic product as contemplated herein leads to longer-lasting deodorizing performance, which means the use of aluminum and aluminum zirconium salts can be avoided.

With regard to other preferred embodiments as contemplated herein, particularly with regard to the agent used or the product used, this applies mutatis mutandis to the statements made about the cosmetic agent as contemplated herein, as well as to the cosmetic product as contemplated herein.

Finally, the last subject-matter of the present disclosure is the use of a mixture of a) at least one aromatic alcohol from Formula (I).

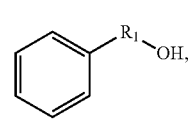

(I)

wherein
$R_1$ stands for on linear $C_1$-$C_{10}$ alkylene group or a branched $C_1$-$C_{10}$ alkylene group.

b) at least one menthyl compound from Formula (II)

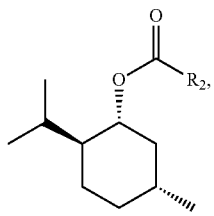

(II)

wherein $R_2$ denotes a $C_1$-$C_4$ alkyl group and to improve the odor-inhibiting effect of cosmetic agents over a period of from about 24 to about 48 hours.

The combination of the alcohol of Formula (I), in particular of 2-methyl-4-phenyl-2-butanol ($R_1$=*—$CH_2$—$CH_2$—$C(CH_3)_2$—**), with at least one menthyl compound of Formula (II), particularly menthyl acetate ($R_2$=*—$CH_3$), leads to a longer-lasting deodorizing effect of cosmetic agents. In addition, in contrast to deodorizing perfume components, these compounds have no allergenic potential. Because of the low inherent smell of this mixture, it is possible to formulate perfume-free cosmetic agents with excellent deodorizing performance, without any allergenic potential and free of aluminum and aluminum zirconium salts.

With regard to other preferred embodiments as contemplated herein, particularly with regard to the alcohol from Formula (I), the menthyl compound from Formula (II) as well as other ingredients of the cosmetic agent, this applies mutatis mutandis to the cosmetic agents, cosmetic product, and also the statements about method as contemplated herein.

The following examples explain the present disclosure without limiting it:

EXAMPLES

The alcohol from Formula (I) used in the following examples is preferably 2-Methyl-4-phenyl-2-butanol ($R_1$=*—$CH_2$—$CH_2$—$C(CH_3)_2$—**), the menthyl compound of Formula (II) more preferably menthyl acetate ($R_2$=*—$CH_3$). Triethyl citrate and/or phenoxyethanol are preferably used as a deodorant agent.

Ethanol-Containing Deodorant Roll-on (all Quantities in Wt. %)

| | 1.1 | 1.2 | 1.3 | 1.4 |
|---|---|---|---|---|
| Alcohol from Formula (I) | 0.4 | 0.2 | 0.1 | 0.5 |
| Menthyl compound from Formula (II) | 0.083 | 0.25 | 0.41 | 0.17 |
| Deodorant agent | 1.5 | 1.5 | 1.5 | 1.5 |
| Hydroxyethylcellulose | 0.4 | 0.4 | 0.4 | 0.4 |
| Ethanol 96% ig | 30 | 30 | 30 | 30 |
| Ceteareth-12 | 2.0 | 2.0 | 2.0 | 2.0 |
| Ceteareth-30 | 2.0 | 2.0 | 2.0 | 2.0 |
| Perfume | 1.0 | 1.0 | 1.0 | 1.0 |
| Water | Ad 100 | Ad 100 | Ad 100 | Ad 100 |

Ethanol-Free Deodorant Roll-on (all Quantities in Wt. %)

| | 2.1 | 2.2 | 2.3 | 2.4 |
|---|---|---|---|---|
| Alcohol from Formula (I) | 0.4 | 0.2 | 0.1 | 0.5 |
| Menthyl compound from Formula (II) | 0.083 | 0.41 | 0.25 | 0.17 |
| Deodorant agent | 0.5 | 0.5 | 0.5 | 0.5 |
| PPG-15 Stearyl ether | 0.5 | 0.5 | 0.5 | 0.5 |
| Steareth-2 | 2.4 | 2.4 | 2.4 | 2.4 |
| Steareth-21 | 1.5 | 1.5 | 1.5 | 1.5 |
| Disodium EDTA | 0.1 | 0.1 | 0.1 | 0.1 |
| Perfume | 1.0 | 1.0 | 1.0 | 1.0 |
| Water | Ad 100 | Ad 100 | Ad 100 | Ad 100 |

Sprayable Deodorant Composition (all Data in Wt. %)

| | 3.1 | 3.2 | 3.3 | 3.4 |
|---|---|---|---|---|
| Alcohol from Formula (I) | 0.4 | 0.2 | 0.1 | 0.5 |
| Menthyl compound from Formula (II) | 0.083 | 0.17 | 0.25 | 0.33 |
| Deodorant agent | 3.0 | 3.0 | 3.0 | 3.0 |
| PEG-40 Hydrogenated Castor Oil | 0.5 | 0.5 | 0.5 | 0.5 |
| Ethanol 96% ig | 55 | 55 | 55 | 55 |
| Perfume | 1.0 | 1.0 | 1.0 | 1.0 |
| Water | Ad 100 | Ad 100 | Ad 100 | Ad 100 |

Ethanol-Containing Deodorant Aerosol (all Data in Wt. %)

| | 4.1 | 4.2 | 4.3 | 4.4 |
|---|---|---|---|---|
| Alcohol from Formula (I) | 0.4 | 0.2 | 0.1 | 0.5 |
| Menthyl compound from Formula (II) | 0.083 | 0.41 | 0.25 | 0.33 |
| Deodorant agent | 6.8 | 6.8 | 6.8 | 6.8 |
| Perfume | 1.0 | 1.0 | 1.0 | 1.0 |
| Ethanol 96% ig | Ad 100 | Ad 100 | Ad 100 | Ad 100 |

Ethanol-Free Deodorant Aerosol (all Data in Wt. %)

| | 5.1 | 5.2 | 5.3 | 5.4 |
|---|---|---|---|---|
| Alcohol from Formula (I) | 0.4 | 0.2 | 0.1 | 0.5 |
| Menthyl compound from Formula (II) | 0.083 | 0.25 | 0.58 | 0.17 |
| Deodorant agent | 6.8 | 6.8 | 6.8 | 6.8 |
| Ethylhexyl palmitate | 18.5 | 18.5 | 18.4 | 18.3 |
| Dimethicone 5 Cst | 10 | 10 | 10 | 10 |
| Perfume | 4.0 | 4.0 | 4.0 | 4.0 |
| Cyclopentasiloxane | Ad 100 | Ad 100 | Ad 100 | Ad 100 |

Aerosol cans were filled with compositions from about 4.1 to about 4.4 as well as from about 5.1 to about 5.4 in the weight ratio of 15:85 with a propellant mixture of propane and n-butane (in the weight ratio 15:85).

All preceding compositions led to an excellent deodorizing effect, which lasted for from about 24 to about 48 hours after the application.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic agent consisting of, relative to the total weight of the cosmetic agent,
   a) at least one aromatic alcohol of Formula (I),

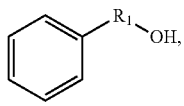
(I)

wherein
$R_1$ stands for a linear $C_1$-$C_{10}$ alkylene group or a branched $C_1$-$C_{10}$ alkylene group, and wherein the at least one aromatic alcohol of Formula (I) includes 2-Methyl-4-phenyl-2-butanol, and wherein the at least one aromatic alcohol of Formula (I) is present in a total quantity of from about 0.010 to about 2.0 wt. %,
   b) at least one menthyl compound of Formula (II)

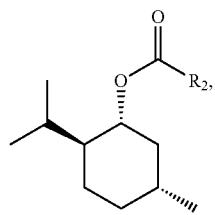
(II)

wherein
$R_2$ denotes a $C_1$-$C_4$ alkyl group, wherein the at least one menthyl compound of Formula (II) includes menthyl acetate, and wherein the at least one menthyl compound of Formula (II) is present in a total quantity of from about 0.01 to about 1.0 wt. %, and wherein the cosmetic agent has a weight ratio of the at least one aromatic alcohol of Formula (I) to the at least one menthyl compound of Formula (II) of from about 200:1 to about 1:100,
   c) at least one deodorant ingredient including triethyl citrate and/or phenoxyethanol,
   d) at least one non-ionic surfactant, wherein the at least one non-ionic surfactant is present in a total quantity of from about 0.0001 to about 15 wt. %,
   e) at least one thickener, wherein the at least one thickener is present in a total quantity of from about 0.1 to about 2.0 wt. %,
   f) at least one chelating agent, wherein the at least one chelating agent is present in a total quantity of from about 0.01 to about 0.5 wt. %, and
   g) at least one cosmetic carrier, wherein the cosmetic agent is free of aluminum and aluminum zirconium salts, wherein all quantities are in relation to the total weight of the cosmetic agent.

2. The cosmetic agent according to claim 1, wherein the at least one deodorant ingredient is present in a total quantity of from about 0.0001 to about 15 wt. %, in relation to the total weight of the cosmetic agent.

3. The cosmetic agent according to claim 1, wherein the at least one aromatic alcohol of Formula (I) is present in a total quantity of from about 0.030 to about 1.0 wt. %, in relation to the total weight of the cosmetic agent.

4. The cosmetic agent according to claim 1, wherein the at least one aromatic alcohol of Formula (I) is present in a total quantity of from about 0.040 to about 0.70 wt. %, in relation to the total weight of the cosmetic agent.

5. The cosmetic agent according to claim 1, wherein the at least one aromatic alcohol of Formula (I) is present in a total quantity of from about 0.050 to about 0.50 wt. %, in relation to the total weight of the cosmetic agent.

6. The cosmetic agent according to claim 1, wherein the at least one menthyl compound of Formula (II) is present in a total amount of from about 0.02 to about 0.80 wt. %, in relation to the total weight of the cosmetic agent.

7. The cosmetic agent according to claim 1, wherein the at least one menthyl compound of Formula (II) is present in a total amount of from about 0.03 to about 0.60 wt. %, in relation to the total weight of the cosmetic agent.

8. The cosmetic agent according to claim 1, wherein the at least one menthyl compound of Formula (II) is present in a total amount of from about 0.05 to 0.50 wt. %, in relation to the total weight of the cosmetic agent.

9. The cosmetic agent according to claim 1, wherein the cosmetic agent has a weight ratio of the at least one aromatic alcohol of Formula (I) to the at least one menthyl compound of Formula (II) of from about 16:1 to about 1:16.

10. Cosmetic agent according to claim 1, wherein the cosmetic agent has a weight ratio of the at least one aromatic alcohol of Formula (I) to the at least one menthyl compound of Formula (II) of from about 6:1 to about 1:12.

11. Cosmetic agent according to claim 1, wherein the cosmetic agent has a weight ratio of the at least one aromatic alcohol of Formula (I) to the at least one menthyl compound of Formula (II) of from about 2:1 to about 1:12.

12. Cosmetic agent according to claim 1, wherein the at least one deodorant ingredient is present in a total quantity of from about 0.001 to about 12 wt. %, in relation to the total weight of the cosmetic agent.

13. A cosmetic agent consisting of, relative to the total weight of the cosmetic agent, a) at least one aromatic alcohol of Formula (I),

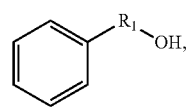
(I)

wherein $R_1$ stands for a linear $C_1$-$C_{10}$ alkylene group or a branched $C_1$-$C_{10}$ alkylene group, and wherein the at least one aromatic alcohol of Formula (I) includes 2-Methyl-4-phenyl-2-butanol, and wherein the at least one aromatic alcohol of Formula (I) is present in a total quantity of from about 0.010 to about 2.0 wt. %, b) at least one menthyl compound of Formula (II)

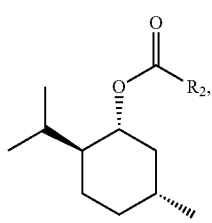 (II)

wherein $R_2$ denotes a $C_1$-$C_4$ alkyl group, wherein the at least one menthyl compound of Formula (II) includes menthyl acetate, and wherein the at least one menthyl compound of Formula (II) is present in a total quantity of from about 0.01 to about 1.0 wt. %, and wherein the cosmetic agent has a weight ratio of the at least one aromatic alcohol of Formula (I) to the at least one menthyl compound of Formula (II) of from about 200:1 to about 1:100, c) at least one deodorant ingredient including triethyl citrate and/or phenoxyethanol, d) at least one non-ionic surfactant, wherein the at least one non-ionic surfactant is present in a total quantity of from about 0.0001 to about 15 wt. %, e) at least one thickener, wherein the at least one thickener is present in a total quantity of from about 0.1 to about 2.0 wt. %, f) at least one chelating agent, wherein the at least one chelating agent is present in a total quantity of from about 0.01 to about 0.5 wt. %, g) at least one cosmetic carrier, wherein the cosmetic agent is free of aluminum and aluminum zirconium salts, and h) at least one propellant, wherein all quantities are in relation to the total weight of the cosmetic agent.

* * * * *